United States Patent
Thornton et al.

(10) Patent No.: US 8,227,016 B2
(45) Date of Patent: Jul. 24, 2012

(54) LAMINATED DRUG-POLYMER COATED STENT WITH DIPPED AND CURED LAYERS

(75) Inventors: Ronan Thornton, Co. Galway (IE); Finbar Dolan, Moate County (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/782,286

(22) Filed: May 18, 2010

(65) Prior Publication Data
US 2010/0228342 A1 Sep. 9, 2010

Related U.S. Application Data

(62) Division of application No. 10/674,296, filed on Sep. 29, 2003, now Pat. No. 7,744,645.

(51) Int. Cl.
*A61L 33/00* (2006.01)
(52) U.S. Cl. ........ 427/2.1; 428/447; 427/387; 427/2.14; 427/2.21; 427/2.24; 427/2.25; 427/430.1; 427/443.2; 427/435; 525/60; 604/265
(58) Field of Classification Search .................. 428/447; 525/60; 604/265; 427/2.1
See application file for complete search history.

(56) References Cited

U.S. PATENT DOCUMENTS

| | | | |
|---|---|---|---|
| 5,380,299 A | 1/1995 | Fearnot et al. | |
| 5,447,724 A | 9/1995 | Helmus et al. | |
| 5,736,251 A * | 4/1998 | Pinchuk | 428/447 |
| 5,980,972 A | 11/1999 | Ding | |
| 6,153,252 A | 11/2000 | Hossainy et al. | |
| 6,214,115 B1 | 4/2001 | Taylor et al. | |
| 6,251,136 B1 | 6/2001 | Guruwaiya et al. | |
| 6,306,166 B1 | 10/2001 | Barry et al. | |
| 6,344,035 B1 | 2/2002 | Chudzik et al. | |

(Continued)

FOREIGN PATENT DOCUMENTS
WO  WO03/099169  12/2003

OTHER PUBLICATIONS

Tao P et al., "Role of Polymers in Improving the Results of Stenting in Coronary Arteries" Biomaterials, Elsevier Science Publishers BV., Barking, GB vol. 17, No. 7., 1996, 685-694.

(Continued)

*Primary Examiner* — Dah-Wei Yuan
*Assistant Examiner* — Andrew Bowman

(57) ABSTRACT

The present invention provides a method of applying a drug-polymer coating on a stent. A stent framework is dipped into a first polymeric solution including a first polymer, a first therapeutic agent, and a first solvent. The polymeric solution is dried and the first polymer is cured to form a thin drug-polymer layer on the stent framework. The steps of dipping the stent framework into the first polymeric solution, drying the first polymeric solution, and curing the first polymer are repeated until a target drug-polymer coating thickness is disposed on the stent framework. A drug-polymer coated stent including a stent framework and a laminated drug-polymer coated stent, a system for treating a vascular condition, and a method of treating a vascular condition are also disclosed.

14 Claims, 7 Drawing Sheets

U.S. PATENT DOCUMENTS

| | | |
|---|---|---|
| 6,358,556 B1 | 3/2002 | Ding et al. |
| 2001/0014717 A1* | 8/2001 | Hossainy et al. ............... 525/60 |
| 2002/0032414 A1 | 3/2002 | Ragheb et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0082685 A1 | 6/2002 | Sirhan et al. |
| 2003/0022216 A1 | 1/2003 | Mao et al. |
| 2003/0216504 A1* | 11/2003 | Woolfson et al. ............. 524/588 |

OTHER PUBLICATIONS

Anonymous: "Porous, Time-Release Mechanism for Silicon-Coated, Drug-Sluting Stent" Research Disclosure, Kenneth Mason Publications, Hampshire, GB, vol. 472, No. 17, Aug. 203.

* cited by examiner

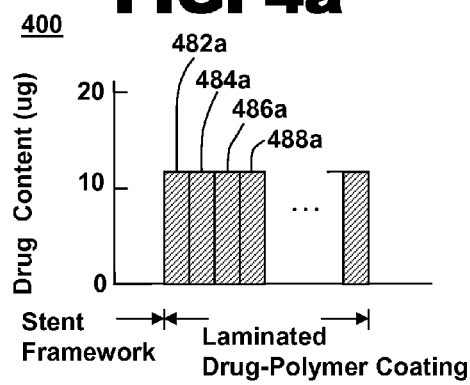
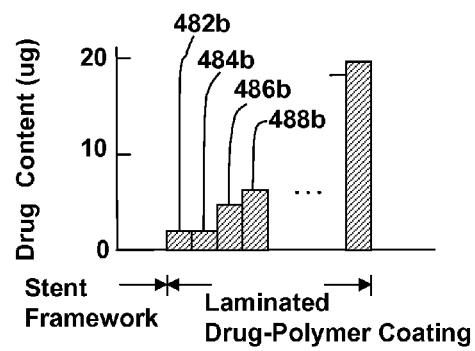
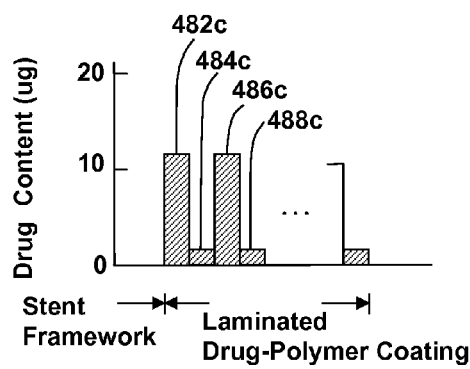
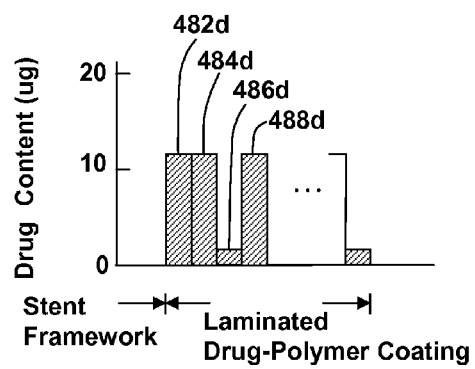
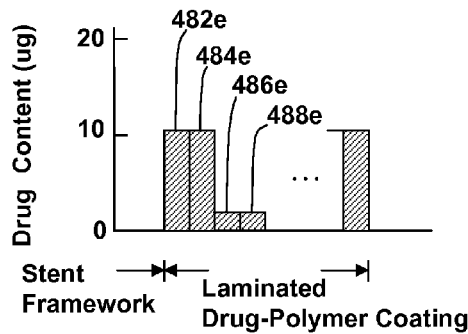

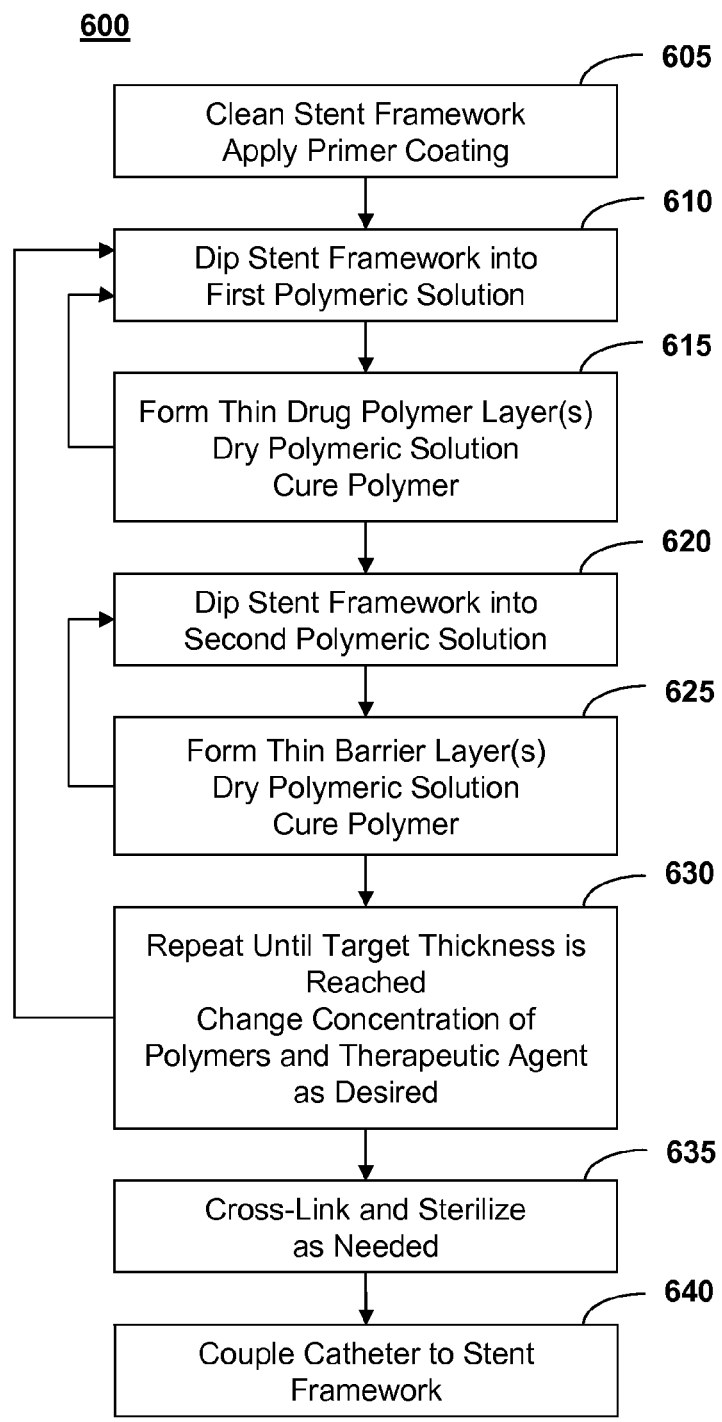

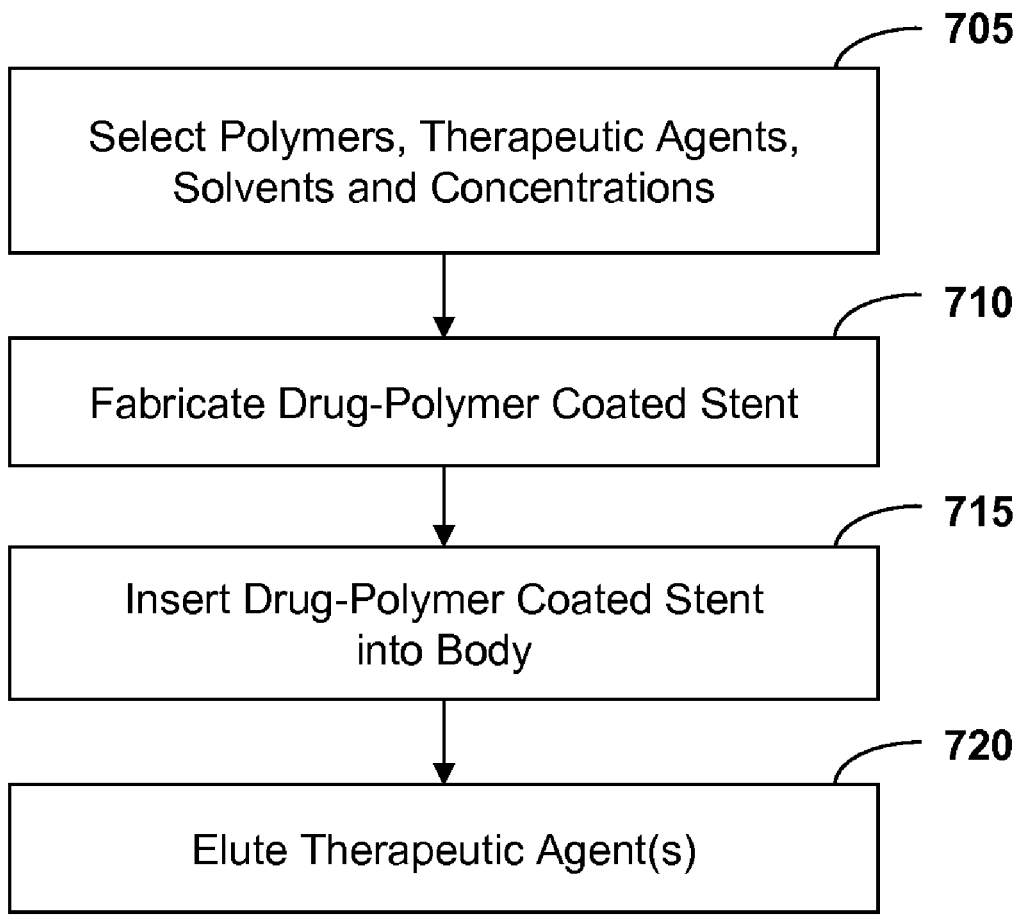

LAMINATED DRUG-POLYMER COATED STENT WITH DIPPED AND CURED LAYERS

RELATED APPLICATIONS

This application is a Division of claims the benefit of U.S. patent application Ser. No. 10/674,296 filed Sep. 29, 2003. The disclosures of which are herein incorporated by reference in their entirety.

FIELD OF THE INVENTION

This invention relates generally to biomedical stents. More specifically, the invention relates to a laminated, multi-layer drug-polymer coating disposed on an endovascular stent for in vivo, time-release drug delivery, and methods of coating thereof.

BACKGROUND OF THE INVENTION

Recent advances in medical procedures such as angioplasty continue to increase the use of endovascular stents in a variety of treatments for unblocking bodily lumens and restoring their function. With generally open tubular structures, stents often have apertured or lattice-like walls of a metallic or polymeric base, and can be either balloon expandable or self-expanding. An exemplary stent is deployed by mounting the stent on a balloon portion of a balloon catheter, positioning the stent in a body lumen, and expanding the stent by inflating the balloon. The balloon is then deflated and removed, leaving the stent in place. Stents help reduce the probability and degree of vessel blockage from restenosis.

Stents coated with protective materials and bioactive drugs are available commercially and have been shown to increase the effectiveness of stenting procedures and to control drug-elution properties. Medical research indicates a greater effectiveness of vascular stents when stents are coated with pharmaceutical drugs that help prevent or treat medical conditions such as restenosis and thrombosis. Stent coatings provide localized therapeutic pharmacological agents and treatment of a vessel at the site being supported by the stent to deliver patent effects at the site where they are most needed. The localized levels of the medications can be elevated, and therefore potentially more effective than orally or intravenously delivered drugs. Furthermore, drugs released from tailored stent coatings can have controlled, timed-release qualities, eluting their bioactive agents over hours, weeks or even months. Stent coatings typically have a drug or active agent, which has been dissolved or dispersed throughout the polymeric material and physically constrained within the polymer made from polyurethane, polyester, polylactic acid, polyamino acid, polyorthoester, or polyphosphate ester. The sustained release of drugs generally relies upon either degradation of the polymer or diffusion through the polymer to control the elution of the compounds.

Stents and other endovascular devices often undergo significant flexion or expansion during their delivery and deployment, and therefore, drug polymers that coat them need to be mechanically pliant. A stent deployed by self-expansion or balloon expansion is accompanied by a high level of bending at portions of the stent framework, which can cause cracking, flaking, peeling, or delaminating of many candidate drug polymers when the stent diameter is increased by threefold or more during expansion. In addition, any step within the process for coating a pre-deployed stent should not cause a drug-polymer to fall off, crystallize or melt. Chudzik and others disclose a flexible coating composition to address the need for pliancy in "Bioactive Agent Release Coating," U.S. Pat. No. 6,344,035 issued Feb. 5, 2002. The bioactive agent or drug is in combination with a mixture of polymers such as poly(butyl methacrylate) and poly(ethylene-co-vinyl acetate). Polymers for use as stent coatings need to demonstrate characteristics of biocompability, good drug release as well as flexibility.

Drug polymers coatings for stents need to have polymer biocompatibility, satisfactory mechanical properties such as durability and integrity during roll down and expansion of the stent, and correct release profiles for the drugs. Coatings with a polymer or combination of a polymer and a pharmaceutical agent or drug can be applied to a stent with application techniques such as dipping, spraying, painting, and brushing.

In many of the current medical device or stent coating methods, a composition of a drug and a polymer in a common solvent is applied to a device to form a substantially uniform layer of drug and polymer. Techniques have been developed to micronize drugs into small particles so that drugs can be suspended in the polymeric solution. While these techniques can be attractive, micronization is often time consuming, and may result in a degradation or loss of desired therapeutic properties of the drug. A method of using micronized drugs and layering a drug-coated stent using pharmacological and polymeric agents is described by Guruwaiya and others in "Method of Layering a Three-Coated Stent Using Pharmacological and Polymeric Agents," U.S. Pat. No. 6,251,136 issued Jun. 26, 2001. A pharmacological agent is applied to a stent in dry, micronized form over a sticky base coating. A membrane-forming polymer, selected for its ability to allow the diffusion of the pharmacological agent therethrough, is applied over the entire stent.

A method of applying drug-release polymer coatings that uses solvents is described in "Method of Applying Drug-Release Coatings," Ding et al., U.S. Pat. No. 5,980,972 issued Nov. 9, 1999. A polymer is dissolved in one solvent and a drug is dissolved or suspended in a similar or different type of solvent. The solutions are applied either sequentially or simultaneously onto the devices by spraying or dipping to form a substantially homogenous composite layer of the polymer and the biologically active material.

Spraying coating is a currently preferred method for coating stents with drug polymers, which can result in a significant amount of drug-polymer spray material lost during the process. When expensive drugs are used in these coatings, the use of spray coating may be costly.

Dip coating was common with early designs of stents and other medical-device designs, which typically had relatively open construction fabricated from wires or from ribbons. Dipped coatings with relatively low coating weights, for example, coatings with about 4% polymer, were used with some occurrences of bridging or webbing of the coating in the open spaces or slots between the structural members of the device. Such coating was performed by manually dipping the stent in a liquid, and then removing the stent and drying it. The dipping process requires care to avoid excess liquid on the stent framework or inconsistent drying of the liquid, otherwise the apertures can become blocked unnecessarily. Applying one thick coating tends to exacerbate webbing and bridging problems. Increasing the solids content of the coating solution also increases webbing and bridging between the struts. Any coating method needs to avoid webbing, as well as control the weight and thickness of the coating.

Researchers and manufacturers of stents recognize the problems of webbing and having excess coating material on stent struts. For example, a manual-dipping process step that blows excessive material off the open framework of a tubular stent is disclosed in "Coating" by Taylor et al., U.S. Pat. No. 6,214,115 issued Apr. 10, 2001. The process addresses the problems of inconsistent drying and blockage of openings. Another dipping process that addresses the issues of blockage and bridging between the stent struts is disclosed by Hossainy and others in "Process for Coating Stents," U.S. Pat. No. 6,153,252 issued Nov. 28, 2000. Flow or movement of the coating fluid through the openings in the perforated medical device is used to avoid the formation of blockages or bridges. The flow system may use a perforated manifold inserted in the stent to circulate the coating fluid, or may place the stent on a mandrel or in a small tube that is moved relative to the stent during the coating process.

Newer stents that are of less open construction, such as catheter-deployed, self-expanding stents are more difficult to coat evenly using a dipping method. Nevertheless, one advantage of dip coating is the possibility of processing a greater number of stents in a more efficient manufacturing process.

A stent with a single coating of least one therapeutic agent is described by Sirhan and Yan in "Delivery or Therapeutic Capable Agents," U.S. Patent Application Number 20020082679 published Jun. 27, 2002. Barry and others describe another polymer composition that can be used for delivering substantially water-insoluble drugs in "Loading and Release of Water-Insoluble Drugs," U.S. Pat. No. 6,306,166 issued Oct. 23, 2001. A medical device is coated with one or more layers of a volatile organic solution comprising a polyvinyl aromatic polymer and the antineoplastic chemotherapy drug such as paclitaxel. In the descriptions of the forementioned coatings, dipping is given as one of the methods for applying the drug-polymer coating to the device, although the publications do not address the potential problem of webbing or bridging in the open areas of stent structures, particularly when multiple coats are applied.

Multiple dips can be used to build up the weight and thickness of the coating, but each subsequent dip may affect the coating already deposited. A coating can re-dissolve in a second coating solution, causing some loss of the first layer of coating. Also, applications of multiple dip coats from low concentration solutions can have the effect of reaching a limiting loading level as equilibrium is reached between the solution concentration and the amount of coating with or without a pharmaceutical agent. One such method that applies a plurality of relatively thin coatings on an open-lattice stent is disclosed in "Drug Release Stent Coating," Ding et al., U.S. Pat. No. 6,358,556 issued Mar. 19, 2002. The stents are coated by dipping or preferably spraying the stent with a solvent mixture of uncured polymeric silicone material with a crosslinker and a finely divided biologically active species. The method includes a step for sterilizing with an inert argon gas plasma and exposure to gamma radiation.

A multiple-dip coating method that uses two or more incompatible polymer solutions to build up successive layers may avoid the load limitations of coating methods that employ one type of solvent, but it may lose the cost and time advantage of dipping coating over other coating techniques. Thus, a more beneficial multiple-dip coating technique for stents would not require the use of incompatible polymer solutions to solve the problem of previous coating layers being dissolved by the next layer of dipped drug polymer.

Accordingly, what is needed is an improved manufacturing method for dip-coating medical devices such as stents that can apply multiple drug-polymer coatings in a time-efficient manner while avoiding the leaching of a drug or polymer from a previous layer by the dipping solution constituents. An improved process provides coatings that are well adhered and flexible, as well as controls coating properties such as thickness, porosity, and smoothness. An improved stent with one or more drug-polymer coatings maintains mechanical integrity during its deployment, provides a desired elution rate for one or more drugs, and overcomes the deficiencies and limitations described above.

SUMMARY OF THE INVENTION

One aspect of the invention provides a method of applying a drug-polymer coating on a stent. A stent framework is dipped into a first polymeric solution including a first polymer, a first therapeutic agent, and a first solvent. A thin drug-polymer layer is formed on the stent framework by drying the first polymeric solution and curing the first polymer. The steps of dipping the stent framework into the first polymeric solution and forming the thin drug-polymer layer are repeated until a target thickness of the drug-polymer coating with the thin drug-polymer layers is disposed on the stent framework.

Another aspect of the invention is a drug-polymer coated stent, including a stent framework and a laminated drug-polymer coating disposed on the stent framework. The laminated drug-polymer coating includes a plurality of thin drug-polymer layers. The thin drug-polymer layers include a first therapeutic agent and a cured first polymer.

Another aspect of the invention is a system for treating a vascular condition, including a catheter and a coated stent coupled to the catheter. The coated stent includes a stent framework and a laminated drug-polymer coating disposed on the stent framework. The laminated drug-polymer coating includes a plurality of thin drug-polymer layers. The thin drug-polymer layers include a first therapeutic agent and a cured first polymer.

Another aspect of the invention is a method of treating a vascular condition. A drug-polymer coated stent is inserted within a vessel of a body. The drug-polymer coated stent includes a laminated drug-polymer coating with a plurality of thin drug-polymer layers. The thin drug polymer layers include at least one therapeutic agent and a cured first polymer. At least one therapeutic agent is eluted from the laminated drug-polymer coating into the body.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein:

FIG. 4a, FIG. 4b, FIG. 4c, FIG. 4d and FIG. 4e are graphs of drug concentration in a laminated drug-polymer coated stent, in accordance with various embodiments of the current invention;

FIG. 6 is a flow diagram of a method of applying a drug-polymer coating on a stent, in accordance with one embodiment of the current invention; and FIG. 7 is a flow diagram of a method for treating a vascular condition, in accordance with one embodiment of the current invention.

DETAILED DESCRIPTION OF THE PRESENTLY PREFERRED EMBODIMENTS

Figure 1:
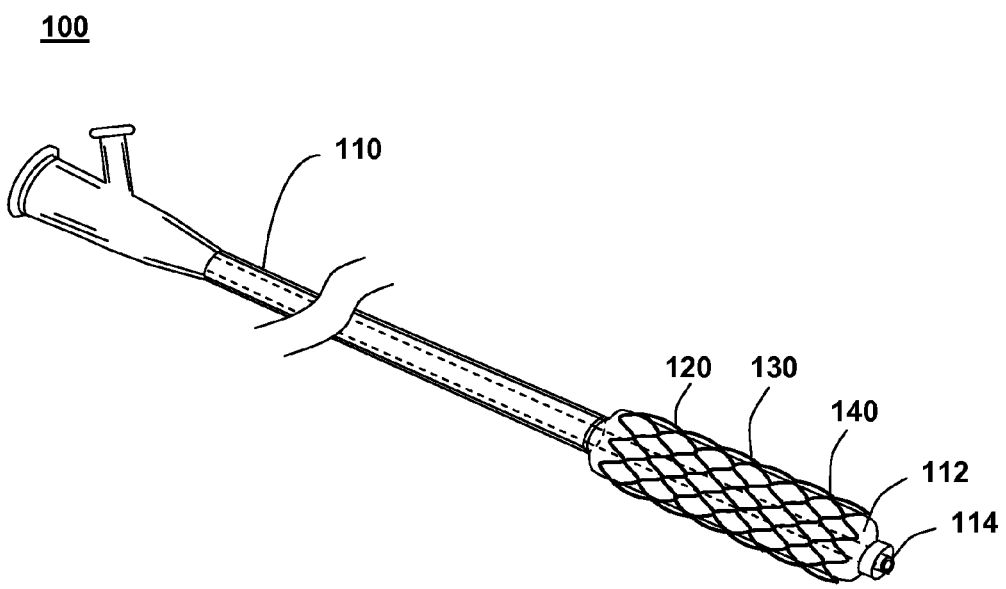
FIG. 1 is an illustration of a system for treating a vascular condition including a drug-polymer coated stent coupled to a catheter, in accordance with one embodiment of the current invention.

FIG. 1 shows an illustration of a system for treating a vascular condition, comprising a drug-polymer coated stent coupled to a catheter, in accordance with one embodiment of the present invention at 100. Vascular treatment system 100 includes a drug-polymer coated stent 120 coupled to a delivery catheter 110. Drug-polymer coated stent 120 includes a stent framework 130 and a laminated drug-polymer coating 140 disposed on the stent framework. Laminated drug-polymer coating 140 includes a plurality of thin drug-polymer layers. The drug-polymer layers include a therapeutic agent and a cured first polymer. Laminated drug-polymer coating 140 may include at least one thin barrier layer positioned between one or more thin drug-polymer layers. The barrier layers include a cured second polymer and may also include a second therapeutic agent. The constituents of coated stent 120 are selected to provide a pre-determined drug-release profile.

Insertion of coated stent 120 into a vessel in the body helps treat, for example, heart disease, various cardiovascular ailments, and other vascular conditions. Catheter-deployed coated stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

Laminated drug-polymer coating 140 includes one or more therapeutic agents. Laminated drug-polymer coating 140 may comprise one or more therapeutic agents dispersed within drug-polymer layers or barrier layers on coated stent 120, which are eluted from coated stent 120 with controlled time delivery after deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Laminated drug-polymer coating 140 may comprise, for example, an antirestenotic agent such as rapamycin, a rapamycin derivative, or a rapamycin analogue to prevent or reduce the recurrence of narrowing and blockage of the bodily vessel. Laminated drug-polymer coating 140 may comprise an anti-cancer drug such as camptothecin or other topoisomerase inhibitors, an anti-inflammatant such as dexamethasone, an anti-proliferant compound such as 5-fluorouracil, a bioactive agent, a pharmaceutical drug, a therapeutic substance, or a combination thereof. The concentration of the therapeutic agent in the drug-polymer layers may be modulated to provide a predetermined drug-release profile.

The elution rates of the therapeutic agents and total drug eluted into the body and the tissue bed surrounding the stent framework are based on the target thickness of laminated drug-polymer coating 140, the constituency and individual layer thicknesses of laminated drug-polymer coating 140, the nature and concentration of the therapeutic agents, the thickness and composition of any cap coat, and other factors. Laminated drug-polymer coating 140 may include and elute multiple therapeutic agents to achieve the desired therapeutic effect. Laminated drug-polymer coating 140 can be tailored to control the elution of one or more therapeutic agents primarily by diffusion processes. In some cases, a portion of the polymeric coating is absorbed into the body, releasing therapeutic agents from within the coating as the polymeric coating is dissolved. The thin barrier layers can be selected to provide a diffusion barrier to the therapeutic agents and to slow drug elution.

Incorporation of a drug or other therapeutic agent into laminated drug-polymer coating 140 allows, for example, the rapid delivery of a pharmacologically active drug or bioactive agent within a day following the deployment of a stent, with a slower, steady delivery of a second bioactive agent over the next three to six months. In one example, a first therapeutic agent comprises an antirestenotic drug such as rapamycin, a rapamycin derivative, or a rapamycin analogue. In another example, the first therapeutic agent comprises an anti-cancer drug such as camptothecin or other topoisomerase inhibitors. In another example, the first therapeutic agent comprises an anti-proliferative compound such as 5-fluorouracil, with an optional second therapeutic agent such as rapamycin, a rapamycin derivative, a rapamycin analogue, or dexamethosone in the barrier layers. In another example, the first therapeutic agent comprises an anti-inflammatant such as dexamethasone, and an optional second therapeutic agent such as 5-fluorouracil. The therapeutic agent constituency in the drug-polymer layers may be, for example, between 0.1 percent and 50 percent of the drug-polymer layer by weight. The therapeutic agent constituency in the barrier layers may be, for example, between 0.1 percent and 50 percent of the barrier layer by weight.

Although more than one therapeutic agent may be combined within a single drug-polymer layer or a single barrier layer, having separated layers with at most one therapeutic agent in each layer to minimized drug-drug interactions is presently preferred. Curing the individual drug-polymer layers and barrier layers during fabrication by polymerization or cross-linking aids in retaining the therapeutic agents within their associated layers until the coated stent is deployed in the body and allows multiple layers of drug-polymer layers and barrier layers to be formed on stent framework 130. Curing, in the context of this specification, refers to either cross-linking or polymerization, or a combination thereof.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a dilute contrast fluid that fills a tube inside catheter 110 and balloon 112. Coated stent 120 is expanded until a desired diameter is reached, and then the contrast fluid is depressurized or pumped out, separating balloon 112 from coated stent 120 and leaving coated stent 120 deployed in the vessel of the body. Alternately, catheter 110 may include a sheath that retracts to allow expansion of a self-expanding version of coated stent 120.

Figure 2A:
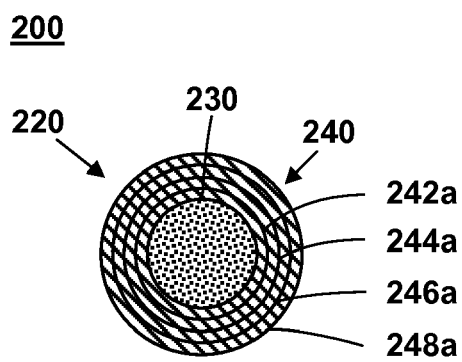
FIG. 2a is a cross-sectional view of a portion of a drug-polymer coated stent, in accordance with one embodiment of the current invention.

FIG. 2a shows a cross-sectional view of a portion of a drug-polymer coated stent, in accordance with one embodiment of the present invention at 200. A drug-polymer coated stent 220 includes a stent framework 230 with a laminated drug-polymer coating 240 disposed on stent framework 230. Laminated drug-polymer coating 240 includes a plurality of thin drug-polymer layers 242a, 244a, 246a and 248a that are positioned on stent framework 230. Drug-polymer layers 242a, 244a, 246a and 248a include a first therapeutic agent and a cured first polymer. Laminated drug-polymer coating 240 may also include one or more barrier layers between one or more drug-polymer layers, one or more of which may also include a second therapeutic second agent.

Although illustrated with four drug-polymer layers, a larger number of drug-polymer layers may be disposed on stent framework 230. For example, ten layers, each layer on the order of 0.1 micrometers thick, can be disposed on stent framework 230 to produce a one-micrometer thick coating. In another example, twenty layers, each layer on the order of 0.5 micrometers thick, can be disposed on stent framework 230 to produce a ten-micrometer thick coating. The drug-polymer layers and any barrier layers need not be the same thickness, and the thickness of each may be varied throughout laminated drug-polymer coating 240. Similarly, the concentration of the pharmaceutical agents may be varied between adjacent layers. Although not shown, the first coating layer may be a primer layer, and the final coating layer may comprise, for example, a thick cap coat.

Stent framework 230 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

In one example, drug-polymer layers 242a, 244a, 246a and 248a comprise a cured first polymer such as a silicone polymer and a first therapeutic agent such as rapamycin, a rapamycin derivative, a rapamycin analogue, camptothecin, dexamethasone, or 5-fluorouracil. Tailoring the polymers, the thickness of the drug-polymer layers, or the concentration of the therapeutic agents controls the elution rate of one or more therapeutic agents dispersed within laminated drug-polymer coating 240. Drug elution refers to the transfer of a therapeutic agent from laminated drug-polymer coating 240 to the surrounding area in a body. The amount of drug eluted is determined as the total amount of therapeutic agent excreted out of laminated drug-polymer coating 240, typically measured in units of weight such as micrograms, or in weight per peripheral area of the stent.

In another example, drug-polymer layers 242a, 244a, 246a and 248a comprise an amphiphilic copolymer from acrylic acid and vinyl pyrollidone, and a first therapeutic agent such as rapamycin, a rapamycin derivative, a rapamycin analogue, camptothecin, dexamethasone, or 5-fluorouracil.

Figure 2B:
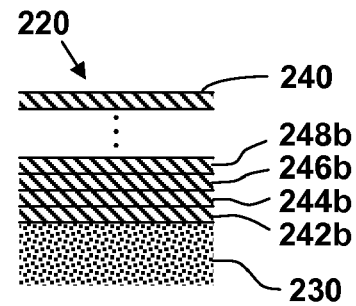
FIG. 2b, FIG. 2c, FIG. 2d and FIG. 2e show enlarged longitudinal cross-sectional views of a portion of a drug-polymer coated stent, in accordance with various embodiments of the current invention.

FIG. 2b shows an enlarged longitudinal cross-sectional view of a portion of a drug-polymer coated stent, in accordance with one embodiment of the present invention. A drug-polymer coated stent 220 includes a stent framework 230 and a laminated drug-polymer coating 240 disposed on stent framework 230. Multiple layers of thin drug-polymer layers 242b, 244b, 246b and 248b comprise a cured first polymer and at least one therapeutic agent within each layer. The thickness, number, and composition of the individual drug-polymer layers and the concentration of the therapeutic agents may be varied within the layers to provide a desired drug-release profile.

Figure 2C:
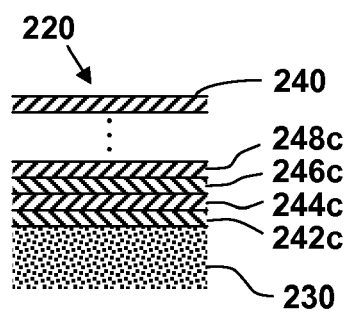

FIG. 2c shows an enlarged longitudinal cross-sectional view of a portion of a drug-polymer coated stent, in accordance with another embodiment of the present invention. A drug-polymer coated stent 220 includes a stent framework 230 and a laminated drug-polymer coating 240 disposed on stent framework 230. Multiple layers of thin drug-polymer layers 242c and 246c comprise a cured first polymer and at least one therapeutic agent within each layer. Positioned between each drug-polymer layer are thin barrier layers 244c and 248c. Barrier layers 244c and 248c comprise a cured second polymer such as a silicone polymer or an amphiphilic copolymer from acrylic acid and vinyl pyrollidone. The barrier layers may also include a second therapeutic agent. The thickness of the individual drug-polymer layers and barrier layers, the number of barrier layers, and the concentration of the therapeutic agents within each drug-polymer layer and barrier layer may be varied to provide a desired drug-release profile.

Figure 2D:
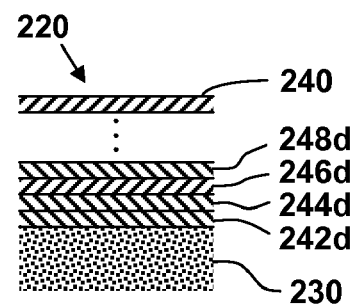

FIG. 2d shows an enlarged longitudinal cross-sectional view of a portion of a drug-polymer coated stent, in accordance with another embodiment of the present invention. A drug-polymer coated stent 220 includes a stent framework 230 and a laminated drug-polymer coating 240 disposed on stent framework 230. In this example, two or more layers of thin drug-polymer layers 242d, 244d and 248d comprise a cured first polymer and at least one therapeutic agent within each layer. Positioned between the sets of drug-polymer layers is a thin barrier layer 246d. The thickness of the adjacent drug-polymer layers and barrier layers, the number of drug-polymer layers and barrier layers, and the concentration of the therapeutic agents within each drug-polymer layer and barrier layer may be varied to provide a desired drug-release profile.

Figure 2E:
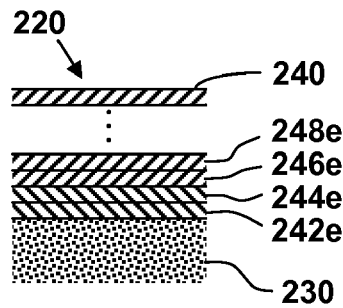

FIG. 2e shows an enlarged longitudinal cross-sectional view of a portion of a drug-polymer coated stent, in accordance with another embodiment of the present invention. A drug-polymer coated stent 220 includes a stent framework 230 and a laminated drug-polymer coating 240 disposed on stent framework 230. In this example, two or more layers of thin drug-polymer layers 242e and 244e comprise a cured first polymer and at least one therapeutic agent within each layer. Positioned between the sets of drug-polymer layers are two or more thin barrier layers 246e and 248e. The thickness and number of drug-polymer layers and barrier layers, the number of layers, and the concentration of the therapeutic agents within each drug-polymer layer and barrier layer may be varied to provide a desired drug-release profile.

Figure 3:
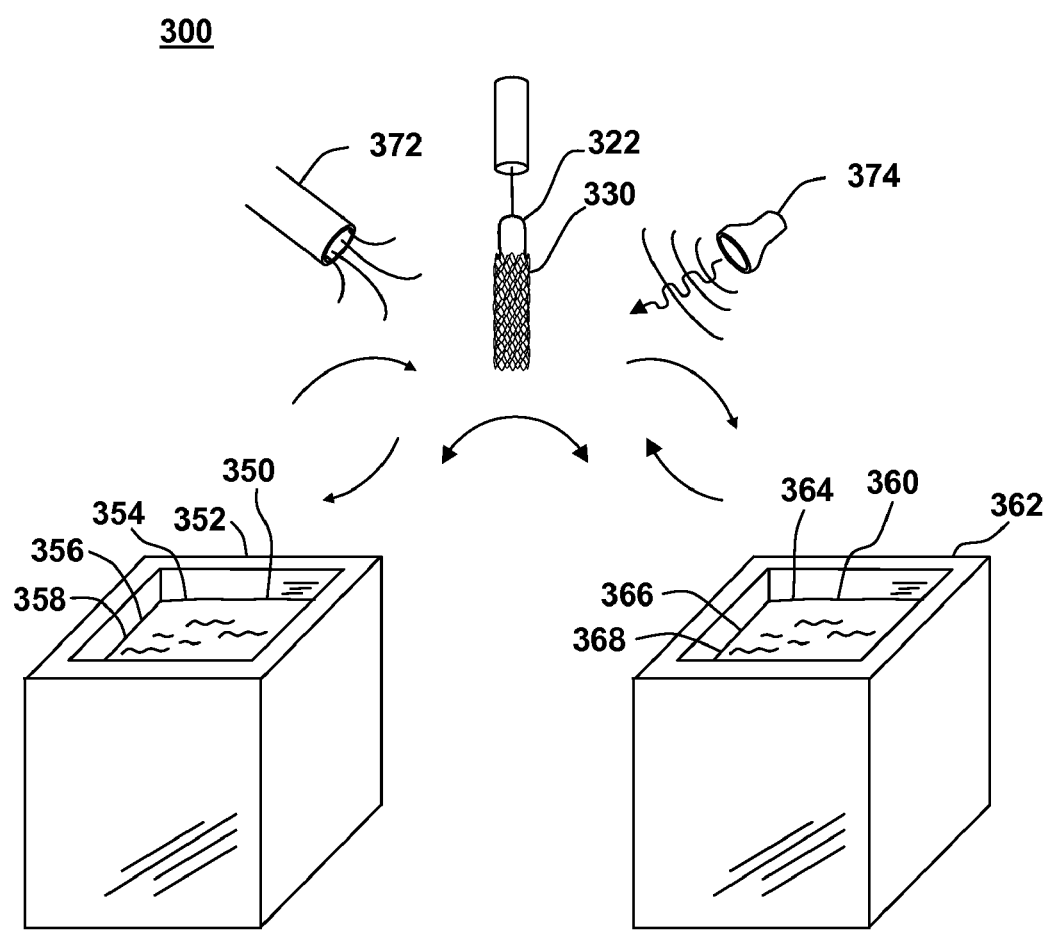
FIG. 3 is an illustration of a system for applying a drug-polymer coating on a stent, in accordance with one embodiment of the current invention.

FIG. 3 shows an illustration of a system for applying a drug-polymer coating on a stent, in accordance with one embodiment of the present invention at 300. Drug-polymer coating system 300 includes a first polymeric solution 350 in a first tank 352, a second polymeric solution 360 in a second tank 362, and a mechanism 322 such as a mandrel, a clamp, or a tether for holding and transporting stents in and out of a tank either manually or automatically. Multiple stent frameworks 330 are readily accommodated for dipping and drying in a batch or continuous batch process.

First polymeric solution 350 includes a first polymer 354, a first therapeutic agent 356, and a first solvent 358. Stent framework 330 can be dipped into first polymeric solution 350 and dried, for example, by positioning dipped stent framework 330 in forced hot air from a hot-air gun 372 and evaporating first solvent 358 to form a thin drug-polymer layer, by spinning off excess fluid, with bursts of air, or with the application of vacuum. The drug-polymer layer is then cured before re-inserting stent framework 330 into first polymeric solution 350 or into second polymeric solution 360. Curing of the drug-polymer layers can be done, for example, using an ultra-violet (UV) light source 374 from a UV bulb or a blade of light from a UV laser placed in or above the baths, or with other methods such as thermal activation, electrical activation with inductively coupled RF energy, or ionizing radiation from an electron beam or a gamma source. The concentration of first polymer 354 in first polymeric solution 350 is set to keep the effective viscosity of the solution low, so that uniform coats of polymer can be applied to stent framework 330, and so that minimal or no bridging occurs across the apertures of stent framework 330. The drug-polymer layers may be cured in-situ. The drug-polymer layers may be effectively patterned on the interior or the exterior of stent framework 330 by selective ultraviolet light or laser light irradiation.

Second polymeric solution 360 includes a second polymer 364 and a second solvent 368. Stent framework 330 with one or more laminated drug-polymer layers can be dipped into second polymeric solution 360 and dried, for example, by positioning dipped stent framework 330 in heated air for high throughput and evaporating second solvent 368 to form a thin barrier layer. The barrier layer is then cured using, for example, ultraviolet light, thermal activation, electrical activation, or ionizing radiation. Second polymeric solution 360 may include a second therapeutic agent 366 dissolved into second solvent 368. Low viscosity for minimizing bridging and webbing across the apertures of stent framework 330 can be obtained by minimizing the solids content in second polymeric solution 360. After dipping stent framework 330 into second polymeric solution 360 and curing the barrier layer, stent framework 330 may be re-inserted into second polymeric solution 360 for an additional barrier layer or re-inserted into first polymeric solution 350 for an additional drug-polymer layer.

The concentration of polymers and therapeutic agents in first polymeric solution 350 and in second polymeric solution 360 can be modulated to provide a predetermined drug-release profile. For example, the concentration of first polymer 354 in first polymeric solution 350 or the concentration of second polymer 364 in second polymeric solution 360 is set higher or lower than previously dipped, dried and cured layers in accordance with the desired thickness profile. Similarly, the concentration of first therapeutic agent 356 in first polymeric solution 350 or the concentration of second therapeutic agent 366 in second polymeric solution 360 may be set higher or lower than previously dipped, dried and cured layers in accordance with the desired drug-concentration profile. Alternately, the therapeutic agent may be changed with subsequent dipping and curing steps so that one or more therapeutic agents in the drug-polymer layers or the barrier layers can be provided.

FIG. 4a shows a graph of drug concentration in a laminated drug-polymer coated stent, in accordance with one embodiment of the present invention at 400. An exemplary coated stent has a laminated drug-polymer coating with a plurality of thin drug-polymer layers 482a, 484a, 486a and 488a. The drug-polymer layers include a therapeutic agent and a cured first polymer. The first polymer is cured between subsequent dipping and drying cycles. In this example, the concentration of the therapeutic agent is constant for each drug-polymer layer. In this exemplary graph, the amount of therapeutic agent in each drug-polymer layer is approximately 12 micrograms of drug. Although four layers and the outermost layer are illustrated, a plurality of layers exceeding ten layers, twenty layers, fifty layers or more may be disposed on the stent framework.

FIG. 4b shows a graph of drug concentration in a laminated drug-polymer coated stent, in accordance with another embodiment of the present invention. The coated stent has a laminated drug-polymer coating with a plurality of thin drug-polymer layers 482b, 484b, 486b and 488b, each drug-polymer layer including a therapeutic agent and a cured first polymer. In this example, the concentration of the therapeutic agent is modulated between each drug-polymer layer. In this exemplary graph, the amount of therapeutic agent in each drug-polymer layer varies from approximately 2 micrograms of drug in the innermost drug-polymer layers to nearly 20 micrograms of drug in the outermost drug-polymer layers.

FIG. 4c shows a graph of drug concentration in a laminated drug-polymer coated stent, in accordance with another embodiment of the present invention. The coated stent has a laminated drug-polymer coating with a plurality of thin drug-polymer layers 482c and 486c, each positioned between thin barrier layers 484c and 488c. The drug-polymer layers include a therapeutic agent and a cured first polymer, and the barrier layers include a cured second polymer. The barrier layers may include a second therapeutic agent. In this example, the concentration of therapeutic agent in the drug-polymer layers is about 12 micrograms, with about 2 micrograms of the same therapeutic agent or a different therapeutic agent in the barrier layers.

FIG. 4d shows a graph of drug concentration in a laminated drug-polymer coated stent, in accordance with another embodiment of the present invention. The coated stent has a laminated drug-polymer coating with a plurality of thin drug-polymer layers 482d and 484d positioned adjacent to a thin barrier layer 486d, followed by additional sets of thin drug-polymer layers 488d. The drug-polymer layers include a therapeutic agent and a cured first polymer, and the barrier layers include a cured second polymer. The barrier layers may include a second therapeutic agent. In this example, the concentration of therapeutic agent in the drug-polymer layers is about 12 micrograms, with about 2 micrograms of the same therapeutic agent or a different therapeutic agent in the barrier layers.

FIG. 4e shows a graph of drug concentration in a laminated drug-polymer coated stent, in accordance with another embodiment of the present invention. The coated stent has a laminated drug-polymer coating with a plurality of thin drug-polymer layers 482e and 484e, each set positioned between a plurality of thin barrier layers 486e and 488e. The drug-polymer layers include a therapeutic agent and a cured first polymer, and the barrier layers include a cured second polymer. The barrier layers may include a second therapeutic agent. In this example, the concentration of therapeutic agent in the drug-polymer layers is about 12 micrograms, with about 2 micrograms of the same therapeutic agent or a different therapeutic agent in the barrier layers.

In one example, the laminated drug-polymer coatings with the cured drug-polymer layers and the cured barrier layers on the coated stent elute at least one therapeutic agent. Alternatively, the laminated drug-polymer coating may include and elute multiple therapeutic agents. The thickness of the individual layers, the types of polymers selected, and the concentration of the therapeutic agents, among other factors, can be tailored to control the elution of one or more therapeutic agents from the coated stent. Elution of therapeutic agents occurs primarily by diffusion processes. In some cases, a portion of the laminated drug-polymer coating is absorbed into the body to release the therapeutic agents. In other cases, a portion of polymeric coating erodes away to release the therapeutic agents.

Figure 5:
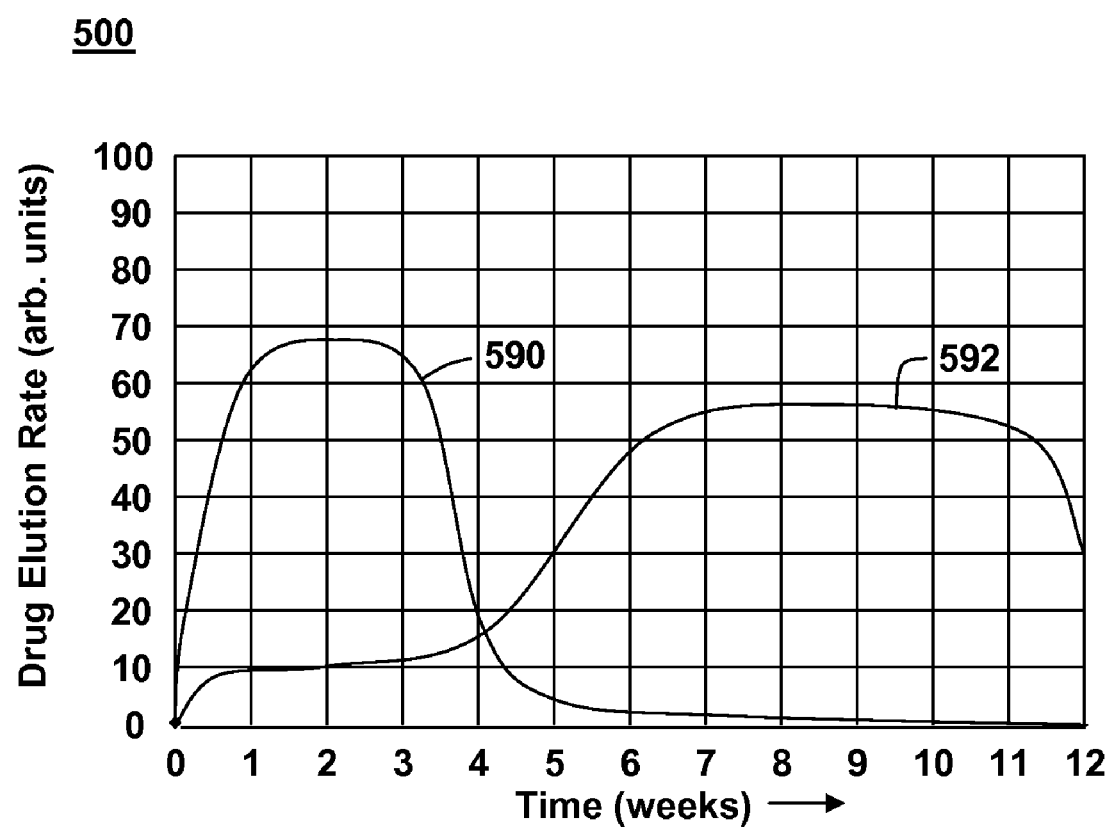
FIG. 5 is a graph of drug elution rate from a drug-polymer coated stent, in accordance with one embodiment of the current invention.

FIG. 5 shows a graph of drug elution rate from a drug-polymer coated stent, in accordance with one embodiment of the present invention at 500. Drug elution rate graph 500 shows a characteristic curve 590 representing the elution of an exemplary first therapeutic agent into the body. After deployment into the body, the first therapeutic agent is eluted from the laminated drug-polymer coating in a predetermined profile, with a large amount of the first therapeutic agent released within the first several weeks, and then the rate of release rapidly falling off after that.

Drug elution rate graph 500 also shows a characteristic curve 592 representing the elution of an exemplary second therapeutic agent into the body after the coated stent is deployed. After deployment into the body, the second therapeutic agent is eluted from the laminated drug-polymer coating in a predetermined profile, with a small amount of the first therapeutic agent released within the first month or so, and increasing to a higher delivery rate in a following period of several months until the therapeutic agent is completely eluted.

An elution rate for each therapeutic agent can be predetermined by a careful selection of the concentration of each therapeutic agent in the thin drug-polymer layers and the thin barrier layers, the thickness of the individual drug-polymer layers and the barrier layers, the polymers and polymeric blend in the drug-polymer layers and the barrier layers, and the total number of layers.

FIG. 6 shows a flow diagram of a method of applying a drug-polymer coating on a stent, in accordance with one embodiment of the present invention at 600. Drug-polymer application method 600 includes various steps to form a laminated drug-polymer coating on a stent framework, and to provide a predetermined drug-release profile when the coated stent is deployed in the body.

A stent framework is cleaned, as seen at block 605. The stent framework may be cleaned, for example, by inserting the stent framework into various solvents, degreasers and cleansers to remove any debris, residues, or unwanted materials from the surface of the stent framework. The stent framework is dried, and generally inspected at this point in the process.

After cleaning, a primer coating may be disposed on the stent framework, particularly to frameworks made of metal such as stainless steel, assisting in the adhesion of the laminated drug-polymer coating to the stent framework. The primer coating may include, for example, the application of a suitable primer layer such as parylene, polyurethane, phenoxy, epoxy, polyimide, polysulfone, pellathane, or silicone. The primer coating may be applied to the stent framework by dipping, spraying, painting, brushing, or other suitable methods. The primer coating is dried and cured or cross-linked as needed for eliminating or removing any volatile components. Excess liquid may be blown off prior to drying the primer coating, which may be done at room temperature or elevated temperatures under a dry nitrogen or other suitable environment such as a vacuum environment.

The stent framework is dipped into a first polymeric solution, as seen at block 610. The first polymeric solution comprises a first polymer, a first therapeutic agent, and a first solvent. One or more therapeutic agents may be mixed with the first polymeric solution prior to its application onto the stent framework. The mixture can be created by adding the therapeutic agents directly into the first polymeric solution. Alternatively, the mixtures can be created by dissolving the therapeutic agents in a therapeutic agent solution comprising a suitable solvent, and then adding and mixing them with the polymeric solution. A first therapeutic agent such as rapamycin, a rapamycin derivative, a rapamycin analogue, camptothecin, dexamethasone, 5-fluorouracil, a bioactive agent, a pharmaceutical drug, a therapeutic substance, or a combination thereof is mixed into the first polymeric solution. The concentration of the therapeutic agent ranges, for example, between 0.1 percent and 50 percent by weight in the dried layer.

The first polymeric solution may comprise, for example, between 0.05 percent and 3.0 percent or more total solids by weight of the first polymer, selected to provide a low-viscosity solution so that very thin layers of the polymer and therapeutic agent may be disposed on the stent framework that can avoid webbing and bridging between the openings in the stent framework. An ultraviolet-sensitive catalyst may be added into the first polymeric solution prior to dipping the stent framework into the first polymeric solution, to aid in the polymerization and cross-linking with subsequent exposure to ultraviolet light. An initiator or a cross-linking agent may be added into the first polymeric solution.

In one example, a hydrophobic silicone coating is built up on the stent framework. A first polymer of low molecular weight silicone oil is combined with a cross-linking agent such as tetrapropylorthosilicate (TPOS) and a catalyst such as stannous octoate. The first solvent in this example is the silicone oil, with the monomer and polymer concentration forming up to 100 percent by volume of the first polymeric solution. Alternatively, the silicone oil may be mixed with isopropyl alcohol or a diluted mixture of isopropyl alcohol and water. A first therapeutic agent such as rapamycin, a rapamycin derivative, a rapamycin analogue, camptothecin, dexamethasone, or 5-fluorouracil is mixed into the first polymeric solution. The rapamycin and associated compounds may be pre-mixed in other solvents, such as acetones, heptanes, methyl tertiary-butyl ether (MTBE), methylene chloride (MEC), tetrahydrofuran (THF), and isopropyl alcohol. The camptothecin is dissolvable and may be pre-mixed in other solvents such as a mixture of ethanol, chloroform and methanol. The dexamethasone may be pre-mixed in a suitable solvent such as tetrahydrofuran. The silicone coating with low molecular weight provides uniform wetting of the stent substrate, and may be used as a primer coating placed directly on a metallic stent framework.

In another example, the first polymeric solution includes a first monomer and polymers of acrylic acid, a second monomer and polymers of vinyl pyrollidone, and an initiator such as benzophenone. The acrylic acid and vinyl pyrollidone may be diluted with an additional solvent such as methanol or a methanol and water mixture. A first therapeutic agent such as rapamycin, a rapamycin derivative, a rapamycin analogue, camptothecin, dexamethasone or 5-fluorouracil is mixed into the first polymeric solution. The therapeutic agents may be pre-mixed in a suitable solvent prior to mixing into the first polymeric solution.

The first polymeric solution is dried and cured to form a thin drug-polymer layer on the stent framework, as seen at block 615. The dipped stent framework may be dried, for example, by positioning the dipped stent framework in air or under forced hot air after dipping the stent framework into the first polymeric solution, and evaporating the first solvent prior to curing the drug-polymer layer and inserting the stent framework in the next polymeric solution. The first polymer is cured, for example, with exposure to ultraviolet light to polymerize or cross-link the monomers or polymers in the solution. Curing of the drug-polymer layers can be done using an ultra-violet light source or with other methods such as thermal activation, electrical activation, or ionizing radiation. Drying refers to either complete or partial removal of the solvent from the layer, resulting in either a dry or a somewhat wet layer. Curing to increase cross-linking, polymerization, or both occurs as the layer is dried.

Additional drug-polymer layers may be applied by re-inserting the stent framework into the first polymeric solution, drying the polymeric solution and curing the first polymer, as seen at blocks 610 and 615, until a target thickness of the drug-polymer coating with the thin drug-polymer layers is disposed on the stent framework. The concentration of the first therapeutic agent in the first polymeric solution may be changed between the dipping, drying and curing steps to modulate the concentration of the first therapeutic agent in the drug-polymer layers and to provide a predetermined drug-release profile.

The stent framework including the one or more drug-polymer layers may be dipped into a second polymeric solution, as seen at block 620. The second polymeric solution includes a second polymer and a second solvent. Because the first drug-polymer layer has been cured, a wider selection of the second solvent is available without excessively dissolving or removing the underlying layers. The stent framework with the first drug-polymer layer can be dipped into the second polymer solution without impacting the content of the initial layer. The concentration of the second polymers in the second polymeric solution may comprise, for example, between 0.05 percent and 3.0 percent or more total solids by weight, selected to provide a low-viscosity solution so that very thin layers of the polymer may be disposed on the stent framework that can avoid webbing and bridging between the openings in the stent framework. An ultraviolet-sensitive catalyst may be added into the second polymeric solution to aid in the polymerization and cross-linking with subsequent exposure to ultraviolet light. An initiator or a cross-linking agent may also be added into the second polymeric solution.

One or more therapeutic agents may be mixed with the second polymeric solution prior to its application onto the stent framework, such as rapamycin, a rapamycin derivative, a rapamycin analogue, camptothecin, dexamethasone, 5-fluorouracil, a bioactive agent, a pharmaceutical drug, a therapeutic substance, or a combination thereof is mixed into the first polymeric solution. The concentration of the therapeutic agent ranges, for example, between 0.1 percent and 50 percent by weight in the dried layer.

In one example, the second polymer solution includes a second polymer of low molecular weight silicone oil combined with a cross-linking agent such as tetrapropylorthosilicate and a catalyst such as stannous octoate. The silicone oil may be mixed with isopropyl alcohol or a diluted mixture of isopropyl alcohol and water, or used without an additional solvent. The molecular weight of the second polymer may be adjusted to provide the desired drug elution rates of the therapeutic agents through the thin barrier coatings. Optionally, a second therapeutic agent such as rapamycin, a rapamycin derivative, a rapamycin analogue, camptothecin, dexamethasone, or 5-fluorouracil is mixed into the second polymeric solution.

In another example, the second polymeric solution includes monomers and polymers of acrylic acid, a second monomer and polymers of vinyl pyrollidone, and an initiator such as benzophenone. The acrylic acid and vinyl pyrollidone may be diluted with an additional solvent such as methanol or a methanol and water mixture to control the viscosity. The length of the resulting copolymer may be adjusted by controlling the amount of initiator and the concentration of the monomers and polymers. A second therapeutic agent such as rapamycin, a rapamycin derivative, a rapamycin analogue, camptothecin, dexamethasone, or 5-fluorouracil may be mixed into the second polymeric solution to provide barrier layers with therapeutic agents.

The second polymeric solution is dried and cured to form a thin barrier layer on the stent framework, as seen at block 625. The cured barrier layer is substantially insoluble in the first polymeric solution, so that when subsequent layers of drug-polymer layers or barrier layers are formed on the stent framework, underlying barrier layers are neither dissolved nor eroded away. The barrier layer may be selected to provide a diffusion barrier to the drug in the drug-polymer layer and to slow down drug elution.

After the stent framework has been dipped into the second polymeric solution, the second polymeric solution may be dried, for example, in air or under forced hot air. The second solvent is evaporated prior to curing the barrier layer and inserting the stent framework in the next polymeric solution. The second polymer is cured, for example, with exposure to ultraviolet light from an ultra-violet light source or with other methods such as thermal activation, electrical activation, or ionizing radiation that polymerize or cross-link the monomers or polymers in the solution. The layer is dried completely or partially to remove solvent from the layer and cured to increase cross-linking, polymerization, or both as the layer is dried.

Additional barrier layers may be applied by re-inserting the stent framework into the second polymeric solution, drying the polymeric solution and curing the second polymer, as seen at blocks 620 and 625. The concentration of the second therapeutic agent in the second polymeric solution may be changed between the dipping, drying and curing steps to modulate the concentration of the second therapeutic agent in the barrier layers and to provide a predetermined drug-release profile.

The steps of dipping the stent framework into the first polymeric solution, drying the first polymeric solution and curing the first polymer, dipping the stent framework into the second polymeric solution, drying the second polymeric solution and curing the second polymer are repeated until a target drug-polymer coating thickness with the thin drug-polymer layers and the thin barrier layers is disposed on the stent framework, as seen at block 630. Multiple dipping and drying steps are used to provide an appropriate coating thickness and amount of therapeutic agents, while avoiding webbing or bridging of the apertures between the struts in the stent framework. Repeated application of thin drug-barrier layers and thin barrier layers allows for uniform, defect-free dip-coated items. The concentration of the therapeutic agents and the polymer concentrations may be changed between the dipping, during and curing steps to modulate the concentration of the therapeutic agents in the thin drug-polymer layers and the thin barrier layers, which results in a predetermined drug-release profile.

Different drug concentrations in the drug-polymer layers can be selected to provide a tailored elution curve, and the barrier layers may help to preserve and prolong the elution of the drugs. Alternatively, the composition of the thin barrier layers can be selected to be highly permeable to one or more of the therapeutic agents, allowing one or more of the therapeutic agents to rapidly elute from the drug-polymer coating, whereas other therapeutic agents elute less rapidly.

The coated stent with the laminated drug-polymer coating may be additionally cross-linked and sterilized as needed, as seen at block 635. Cross-linking may be accomplished by providing additional drying cycles in air, or by heating the coated stent above a curing temperature in an oven with a controlled ambient such as vacuum, nitrogen, or air. Sterilization may employ, for example, gamma-ray irradiation, e-beam radiation, ethylene oxide gas, or hydrogen peroxide gas plasma sterilization techniques. The coated stent may be packaged, shipped, and stored in a suitable package before its clinical use.

A delivery catheter may be coupled to the coated stent, as seen at block 640. An exemplary delivery catheter includes an inflatable balloon that is positioned between the coated stent and the catheter and used for deploying the coated stent in the body. Alternatively, the delivery catheter includes a sheath that retracts to deploy a self-expanding version of the coated stent.

In one exemplary method, fully processed coated stents are reduced in diameter and placed into the distal end of the catheter to form an interference fit, which secures the stent onto the catheter. The catheter with the stent may be placed in a catheter package and sterilized prior to shipping and storing. Before clinical use, the stent is sterilized by any appropriate or medically conventional means.

Alternative ordering of process steps or variants of the method for applying a drug-polymer coating on a stent can be employed. For example, a barrier layer can be applied to the stent framework before a drug-polymer layer by dipping the framework into the second polymeric solution before dipping it into the first polymeric solution. Other embodiments of the present invention include dipping multiple times into the same bath and curing after each dip to thicken a layer, dipping the coated stent into baths with modified concentrations of monomers and polymers to achieve a desired drug-polymer layer thickness and barrier layer thickness, dipping the coated stent into additional baths with adjusted concentrations of therapeutic agents to achieve a desired elution profile, or adjusting the temperature of each bath.

FIG. 7 shows a flow diagram of a method for treating a vascular condition, in accordance with one embodiment of the present invention at 700. Vascular condition treatment method 700 includes steps to insert a drug-polymer coated stent within a vessel of a body and to elute at least one therapeutic agent from the drug-polymer coated stent into the body. One or more therapeutic agents are included or interdispersed within thin drug-polymer layers of the laminated drug-polymer stent coating. The drug-polymer coated stent includes at least one thin barrier layer positioned between one or more thin drug-polymer layers. The thin barrier layers include a cured second polymer.

The first and second polymers and their respective concentrations are selected based on a predetermined elution rate of each therapeutic agent, as seen at block 705. The polymers are also selected to prevent dissolution of dried and cured polymers of previously applied layers with subsequent dipping into polymeric solutions. The fractional constituencies of the polymers and therapeutic agents are selected to achieve an intended pharmaceutical intent, such as a predetermined elution rate for one or more therapeutic agents within the laminated drug-polymer coating. One or more therapeutic agents are included in the drug-polymer layers, and one or more therapeutic agents may be included in the barrier layers. The polymers of the laminated drug-polymer layers and barrier layers are selected based on a predetermined elution rate of each therapeutic agent and the total quantity of each drug delivered. The solvents are selected to effectively form the drug-polymer layers and the barrier layers without undue dissolution of underlying cured polymers and therapeutic agents.

A coated stent with a laminated drug-polymer coating is fabricated by using selected polymers, therapeutic agents, solvents and concentrations thereof, as seen at block 710. The laminated drug-polymer coating has a plurality of thin drug-polymer layers. The drug-polymer layers include a therapeutic agent and a cured first polymer. One or more thin barrier layers including a second polymer may be placed on top of or between one or more drug-polymer layers. A primer coating may be included to improve the adhesion between the stent framework and the coating layers. A cap coat may be placed on the laminated drug-polymer coating to protect the underlying layers.

When ready for deployment, the drug-polymer coated stent having the selected polymers, therapeutic agents, solvents and concentrations is inserted into a vessel of the body, as seen at block 715. The drug-polymer coated stent is inserted typically in a controlled environment such as a catheter lab or hospital. A delivery catheter, which helps position the drug-polymer coated stent in a vessel of the body, is typically inserted through a small incision of the leg and into the femoral artery, and directed through the vascular system to a desired place in the vessel. Guide wires threaded through an inner lumen of the delivery catheter assist in positioning and orienting the drug-polymer coated stent. The position of the drug-polymer coated stent may be monitored, for example, with a fluoroscopic imaging system or an x-ray viewing system in conjunction with radiopaque markers on the coated stent, radiopaque markers on the delivery catheter, or contrast fluid injected into an inner lumen of the delivery catheter and into an inflatable catheter balloon that is coupled to the drug-polymer coated stent. The stent is deployed, for example, by expanding the stent with a balloon or by extracting a sheath that allows a self-expandable stent to enlarge after positioning the stent at a desired location within the body. Before clinical use, the stent is sterilized by using conventional medical means.

Once deployed, the therapeutic agents in the laminated drug-polymer coating are eluted, as seen at block 720. The elution rates of the selected therapeutic agents into the body and the tissue bed surrounding the stent framework are based on the polymers, thickness of the drug-polymer layers and barrier layers, and the concentration of the therapeutic agents contained therein, among other factors.

Although the present invention applies to cardiovascular and endovascular stents with timed-release therapeutic agents, the use of laminated drug-polymer coatings may be applied to other implantable and blood-contacting biomedical devices such as coated pacemaker leads, microdelivery pumps, feeding and delivery catheters, heart valves, artificial livers and other artificial organs.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method of applying a drug-polymer coating on a stent, comprising:
   dipping a stent framework into a first polymeric solution, wherein the first polymeric solution comprises a first polymer, a first therapeutic agent, and a first solvent, the first polymeric solution further comprising a first monomer including acrylic acid, a second monomer including vinyl pyrollidone, and an initiator;

partially drying the first polymeric solution on the stent framework to partially remove the first solvent;

curing the partially dried first polymeric solution to form a thin drug-polymer layer on the stent framework; and repeating the steps of dipping the stent framework into the first polymeric solution, partially drying the first polymeric solution on the stent framework, and curing the partially dried first polymeric solution until a target thickness of the drug-polymer coating with the thin drug-polymer layers is disposed on the stent framework.

2. The method of claim 1 wherein the initiator comprises benzophenone.

3. The method of claim 1 wherein the first polymeric solution comprises between 0.05 percent and 3.0 percent total solids by weight of the first polymer.

4. The method of claim 1 wherein the first therapeutic agent is selected from the group consisting of rapamycin, a rapamycin derivative, a rapamycin analogue, camptothecin, dexamethasone, 5-fluorouracil, a bioactive agent, a pharmaceutical drug, a therapeutic substance, and a combination thereof.

5. The method of claim 1 wherein forming the thin drug-polymer layer comprises drying the first polymeric solution and curing the first polymer with ultraviolet light.

6. The method of claim 1 wherein forming the thin drug-polymer layer comprises drying the first polymeric solution and curing the first polymer with one of thermal activation, electrical activation, or ionizing irradiation.

7. The method of claim 1 further comprising:
adding an ultraviolet-sensitive catalyst into the first polymeric solution prior to dipping the stent framework into the first polymeric solution.

8. The method of claim 1 further comprising:
adding one of the initiator or a crosslinking agent into the first polymeric solution prior to dipping the stent framework into the first polymeric solution.

9. The method of claim 1 further comprising:
dipping the stent framework including the formed thin drug-polymer layer into a second polymeric solution, wherein the second polymeric solution comprises a second polymer and a second solvent;

forming a thin barrier layer on the formed thin drug-polymer layer, wherein the second polymeric solution is dried and wherein the second polymer is cured; and repeating the steps of dipping the stent framework into the first polymeric solution and forming an additional thin drug-polymer layer, and dipping the stent framework including the additional thin drug-polymer layer and forming the thin barrier on the thin drug polymer layer, until a target thickness of the drug-polymer coating with the thin drug-polymer layers and the thin barrier layers is disposed on the stent framework.

10. The method of claim 9 wherein the second polymeric solution comprises a second therapeutic agent.

11. The method of claim 10 wherein the second therapeutic agent is selected from the group consisting of rapamycin, a rapamycin derivative, a rapamycin analogue, camptothecin, dexamethasone, 5-fluorouracil, a bioactive agent, a pharmaceutical drug, a therapeutic substance, and a combination thereof.

12. The method of claim 1 further comprising:
modulating a concentration of the first therapeutic agent in the thin drug-polymer layers to provide a predetermined drug-release profile.

13. A method of applying a drug-polymer coating on a stent, comprising:
dipping a stent framework into a first polymeric solution, wherein the first polymeric solution comprises a first polymer, a first therapeutic agent, and a first solvent, the first polymeric solution further comprising a first monomer including acrylic acid, a second monomer including vinyl pyrollidone, and an initiator;

forming a first thin drug-polymer layer on the stent framework, wherein the first polymeric solution is dried and wherein the first polymer is cured;

repeating the dipping the stent framework and the forming the first thin drug-polymer layer to form a first drug-polymer coating having a first drug-polymer coating target thickness disposed on the stent framework, the first drug-polymer coating including the first thin drug-polymer layer;

dipping the stent framework including the first drug-polymer coating into a second polymeric solution, wherein the second polymeric solution comprises a second polymer and a second solvent;

forming a thin barrier layer on the first drug-polymer coating, wherein the second polymeric solution is dried and wherein the second polymer is cured;

repeating the dipping the stent framework including the first drug-polymer coating and the forming the thin barrier layer to form a barrier coating having a barrier target thickness disposed on the first drug-polymer coating, the barrier coating including the thin barrier layer;

dipping the stent framework including the barrier coating into a third polymeric solution, wherein the third polymeric solution comprises a third polymer, a third therapeutic agent, and a third solvent;

forming a second thin drug-polymer layer on the barrier coating, wherein the third polymeric solution is dried and wherein the third polymer is cured; and repeating the dipping the stent framework including the barrier coating and the forming the second thin drug-polymer layer to form a second drug-polymer coating having a second drug-polymer coating target thickness disposed on the stent framework, the second drug-polymer coating including the second thin drug-polymer layer;

wherein the cured second polymer excludes drug interaction between the first thin drug-polymer layer adjacent the barrier coating and the second thin drug-polymer layer adjacent the barrier coating.

14. The method of claim 13 further comprising:
modulating at least one of a concentration of the first therapeutic agent in the first thin drug-polymer layers and a concentration of the second therapeutic agent in the second thin drug-polymer layers to provide a predetermined drug-release profile.

* * * * *